(12) United States Patent
Brett et al.

(10) Patent No.: US 7,406,386 B2
(45) Date of Patent: Jul. 29, 2008

(54) SYSTEM AND METHOD FOR SENSING AND INTERPRETING DYNAMIC FORCES

(75) Inventors: Peter Brett, Birmingham (GB); Anthony Molloy, Birmingham (GB); Xianghong Ma, Birmingham (GB)

(73) Assignee: Aston University (GB)

( * ) Notice: Subject to any disclaimer, the term of this patent is extended or adjusted under 35 U.S.C. 154(b) by 0 days.

(21) Appl. No.: 10/563,675

(22) PCT Filed: Jul. 9, 2004
(Under 37 CFR 1.47)

(86) PCT No.: PCT/GB2004/002963

§ 371 (c)(1),
(2), (4) Date: Oct. 10, 2006

(87) PCT Pub. No.: WO2005/005947

PCT Pub. Date: Jan. 20, 2005

(65) Prior Publication Data

US 2007/0192045 A1    Aug. 16, 2007

(30) Foreign Application Priority Data

Jul. 9, 2003    (GB) ............................ 0316002.5

(51) Int. Cl.
*G06F 19/00* (2006.01)
(52) U.S. Cl. .................... 702/41; 340/286.01
(58) Field of Classification Search .......... 702/41, 702/182–185, 81, 84, 108, 117, 118, 176, 702/178, 179, 186, 187; 340/286.01, 286.02; 455/405, 423, 67.4; 714/25–27, 31, 57; 709/224–226
See application file for complete search history.

(56) References Cited

U.S. PATENT DOCUMENTS

| | | | |
|---|---|---|---|
| 5,445,020 A | 8/1995 | Rosensweig | |
| 6,788,295 B1 | 9/2004 | Inkster | |
| 2002/0130673 A1* | 9/2002 | Pelrine et al. | 324/727 |
| 2003/0079549 A1 | 5/2003 | Sathya et al. | |

FOREIGN PATENT DOCUMENTS

JP    2002082005    3/2002

* cited by examiner

*Primary Examiner*—Edward Raymond
(74) *Attorney, Agent, or Firm*—Beyer Law Group LLP

(57) ABSTRACT

The present invention relates to a sensing system which is capable of discriminating types of causes of changing loads on a surface, such as the type of motion of a human subject. The system has wide ranging applications including sports performance (e.g. golf club swing analysis). The system comprises a deformable load bearing surface (2), a plurality of mutually spaced sensors (6), a processor (8) and an output (10). The sensors (6) are coupled through the deformation response of the surface (2) to an applied load (4) to receive local sensory data from the surface (2). The processor (8) is operatively coupled to the sensors (6) and is arranged to transform the sensory data into information data relating to a load (4) applied to the surface (2), e.g. by means of a neural network algorithm. In an alternative embodiment, a housing including the deformable load bearing surface (2) contains a flowable material (e.g. liquid) which flows in response to the deformation of the surface.

18 Claims, 4 Drawing Sheets

SYSTEM AND METHOD FOR SENSING AND INTERPRETING DYNAMIC FORCES

Figure 1:
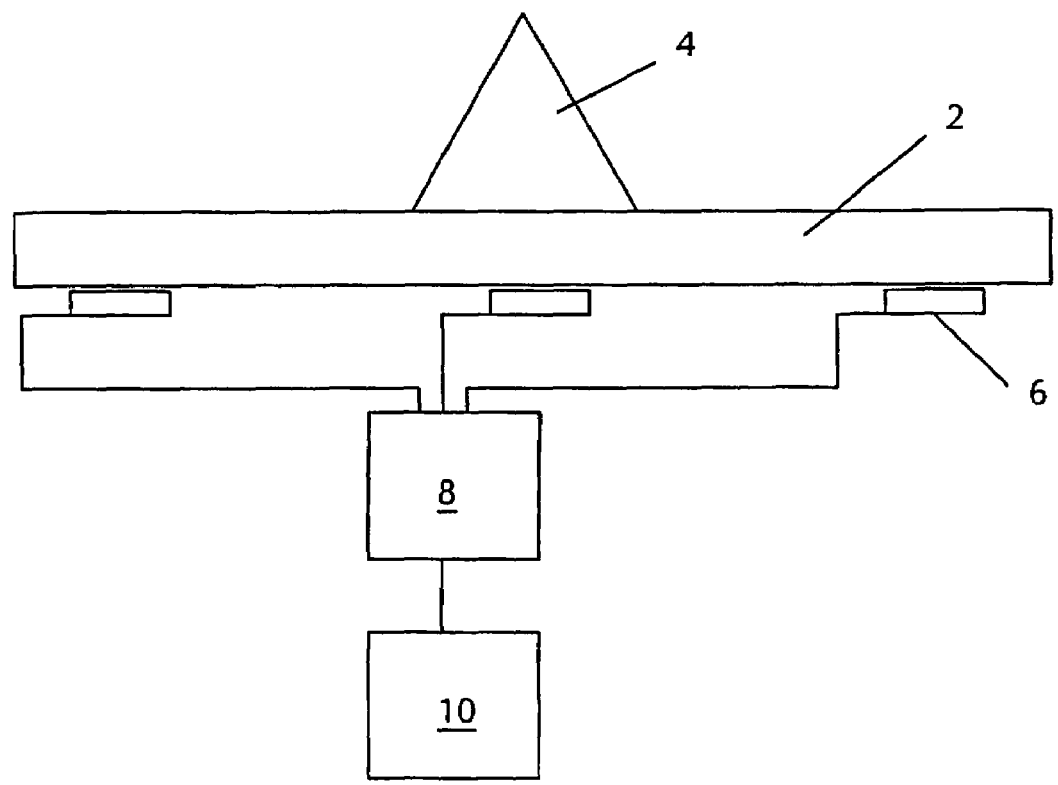

The present application claims priority under 35 U.S.C. 371 to International Application No. PCT/GB2004/002963, the entire disclosure of which is incorporated herein by reference for all purposes.

The present invention relates to a sensing system, particularly a system capable of sensing and interpreting dynamic forces.

There are a range of force sensing systems that can be employed to measure contact forces in a tactile process. There are point force sensors that include single axis or multi-axis force sensing devices that can detect the force acting through a known point. By deploying point force sensing elements to the corners of a rigid flat plate, it is possible to produce a force plate that can be used to evaluate the magnitude and position of the centroid of a contacting force. Force array surfaces can determine the contact impression of new objects through the determination of forces applied to a matrix of discrete point force sensing elements. The positional resolution of such arrays depends directly on the separation of the individual sensing elements. Both force plates and arrays can be manufactured to determine shear force in addition to normal force components to a surface. These systems can be employed to detect both static and transient forces, and arrays can be employed to evaluate distributive contact conditions. Array sensors and multi-axis sensors are of complex construction with many electrical connections. The limit to the spatial resolution of array sensors is based on the minimum scale of micro-fabrication of the surface embodying the sensing elements and the many conductive tracks and connectors to transmit signals to the outside world.

It is an object of the present invention to provide an improved sensing system which obviates or mitigates at least one of the disadvantages of the prior art sensing systems.

According to the present invention there is provided a sensing system comprising:

a deformable load bearing surface, a plurality of mutually spaced sensors, said sensors being coupled through the deformation response of the surface to an applied load whereby to receive local sensory data from said surface, a processor operatively coupled to said sensors and arranged to receive said sensory data from the sensors and to transform said sensory data into information data relating to a load applied to the surface, and an output for outputting the information data, wherein the processor is arranged to process the sensory data received by all the sensors collectively.

It will be understood that by collective processing of the sensory data is meant that the sensory data from each sensor is combined with the sensory data from each of the other sensors and the information data is derived from the combined sensory dataset. In other words, the information data is not derived from a simple sum or product of the individually processed sensory data from each sensor, but collectively in a non-linear fashion to manufacture an output. As each sensor output is affected by the applied load anywhere over the surface, the positioning of the sensors need only be determined to optimise the discrimination between variations in the applied load. Thus, the importance of the deformation in the sense of the surface continuum is that there is coupling between sensor outputs and that the effects of loading anywhere on the surface are transmitted to all individual sensors by the response of the surface. This is in contrast with array sensors where sensing elements respond only to loads applied at the same points as the sensing elements.

The information data may have a linear or a non-linear relationship with the sensory data. The information data may have a non-linear relationship with the processor output.

The number of sensors varies according to the nature of the information to be determined. However, the non-linearity allows complex information to be determined using relatively fewer sensors than would be required in a standard sensor array. Typically, the system has 3 to 10 sensors, preferably 4 to 8 sensors and most preferably 4 to 6 sensors. It will be understood that although fewer sensors are required for the functioning of the system, it may be desirable to provide more sensors than is strictly necessary (redundancy) to increase the robustness of the system and to allow for failure of some sensors, whereupon the remainder can be used to infer the information data corresponding to the applied load.

Preferably, said sensors are transducers, and are more preferably transducers which convert mechanical forces into electrical signals. For example, the sensors may detect strain, in which case resistive, optical, hall effect or capacitance-based transducers may be used; or deformation or deflection, in which case proximity, pressure differential, optical or capacitance-based transducers may be used.

The transducers may be physically connected to or in contact with the surface, e.g. in the case of resistive or variable reluctance transducers where an arm of the transducer is connected to or biased into contact with the surface. Alternatively, there may be no physical contact between the sensors and the surface, e.g. in the case of capacitance, pressure or optical transducers.

The information data is used in conjunction with a processing algorithm that may relate to static or transient load centroid value, load orientation, contact shape. It may relate to object recognition or dynamic information such as frequency, velocity or cadence. The system may comprise a display device for displaying the information data (which may require conversion to a user-readable form). Alternatively, or in addition, the output of the system may serve as an input for a logging system or an automated system for controlling a specific process.

Preferably, the processor incorporates an algorithm or other interpretation function, such as a neural network (e.g. a stochastic back-propagation trained network such as an MLP) or a matrix manipulation technique which receives the sensory data and applies a non-linear transform to produce the information data. The processor may additionally or alternatively incorporate other non-linear transform components.

The deformable load bearing surface is preferably resiliently deformable and/or elastic. Suitable materials include rubber, plastics, metal and wood. The surface may be a laminate of two or more materials. The surface may be in the form of a flat sheet (planar) or alternatively moulded into a desired configuration. Deformation may be by a variety of mechanisms in response to shear, tensile and/or bending forces.

The deformable load bearing surface preferably forms part of a housing, the sensors preferably being sealed therein. Sealing the sensors within the housing avoids exposing the sensors to the external environment, thereby prolonging their operational lifespan and the physical robustness of the system to harsh environmental conditions.

In an alternative (preferred) embodiment, the housing contains a flowable material (e.g. liquid) which flows within or under the surface as part of the mechanism of the deformation response of the surface. The sensors are arranged to detect pressure differentials due to the flow of material. The housing may also comprise one or more flow restrictors which affect the flow characteristics of the flowable material upon deformation of the surface. For example, the flowable material may be flowable within a porous material which partially or completely fills the housing. In a slight variation of the above preferred embodiment, the sensors are arranged to measure changes in distance between the surface and another part of the housing, e.g. its base.

For many applications the surface is conveniently flat. However, the system is not constrained to flat surfaces and the surface can be of any shape dependent upon its intended use.

The present invention also resides in a method of characterising a load applied to a load bearing surface comprising the steps of:
(i) generating sensory data about the surface from a plurality of sensing elements operably coupled with the surface,
(ii) combining the sensory data into a single vector of inputs for a non-linear transformation,
(iii) applying a non-linear transformation to the vector of inputs whereby to generate information data characterising the load, and
(iv) outputting the information data.

The output information may be, for example, information describing a contacting object, its state or its motion.

Steps (ii) and (iii) are preferably performed by a programmed computer. Hence the invention further resides in a carrier medium carrying a computer executable software program for controlling a computer to carry out steps (ii) and (iii) of the method of the present invention.

Preferably, the carrier medium is a storage medium, such as a floppy disk, CD-ROM, DVD or a computer hard drive. Although it will be understood that the carrier medium may also be a transient carrier e.g. an electrical or optical signal.

Figure 2:
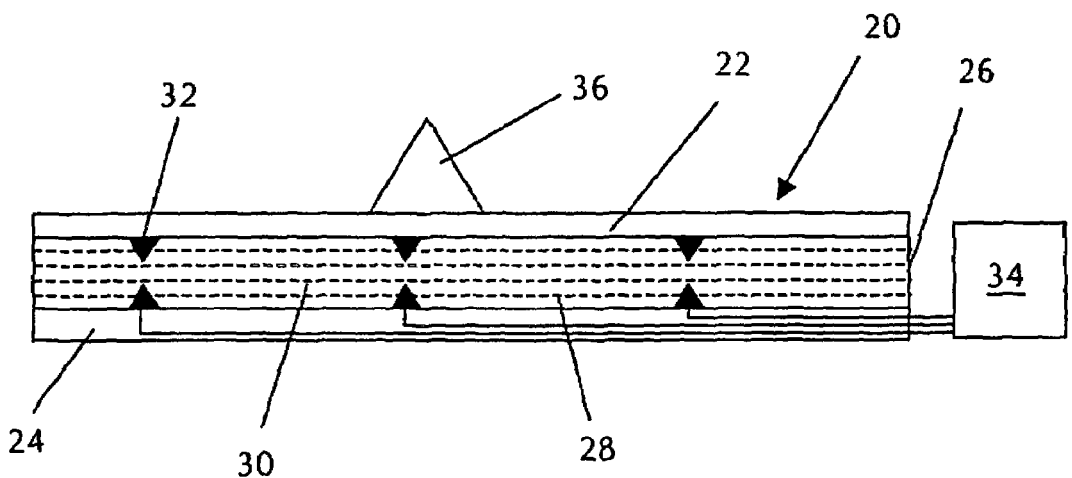
Figure 3:
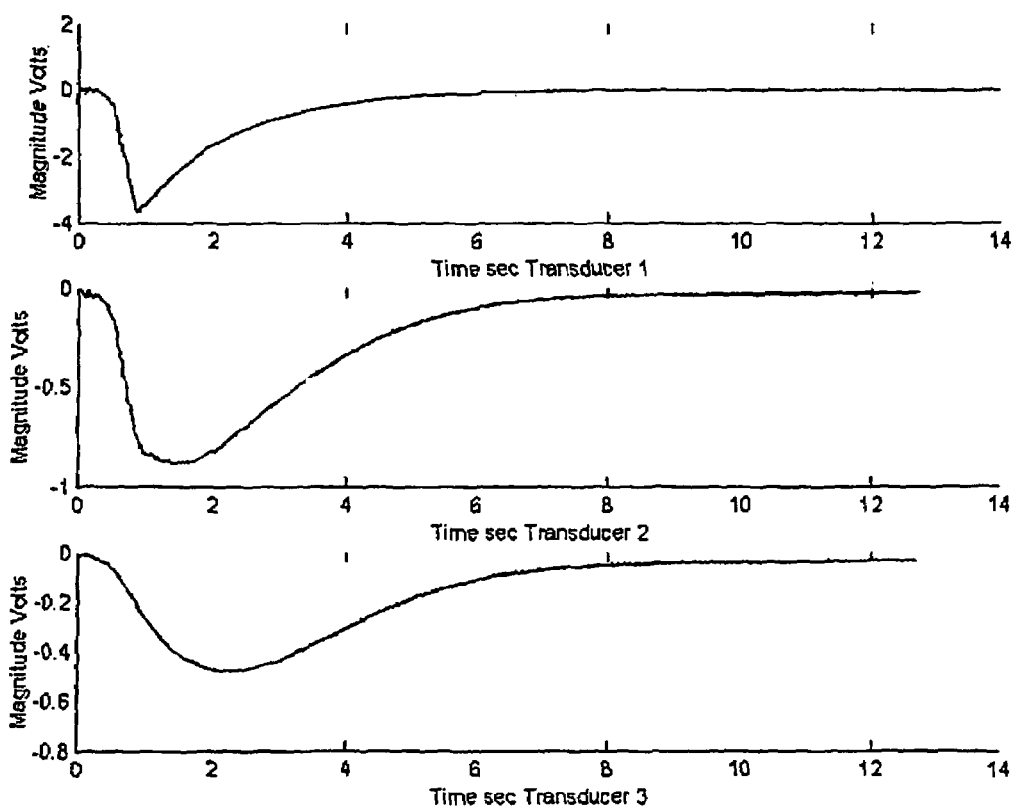
Figure 4:
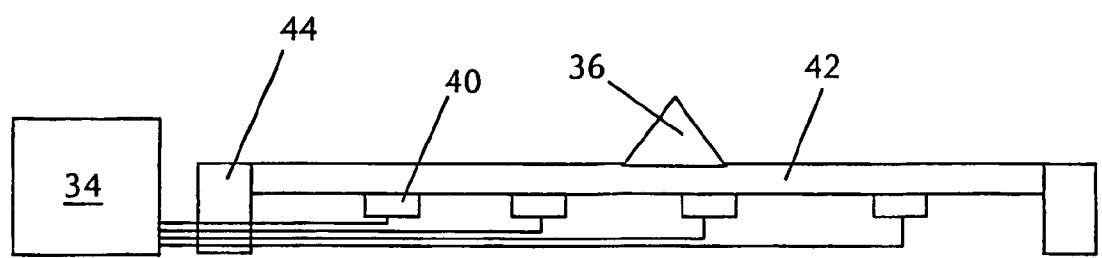
Figure 5:
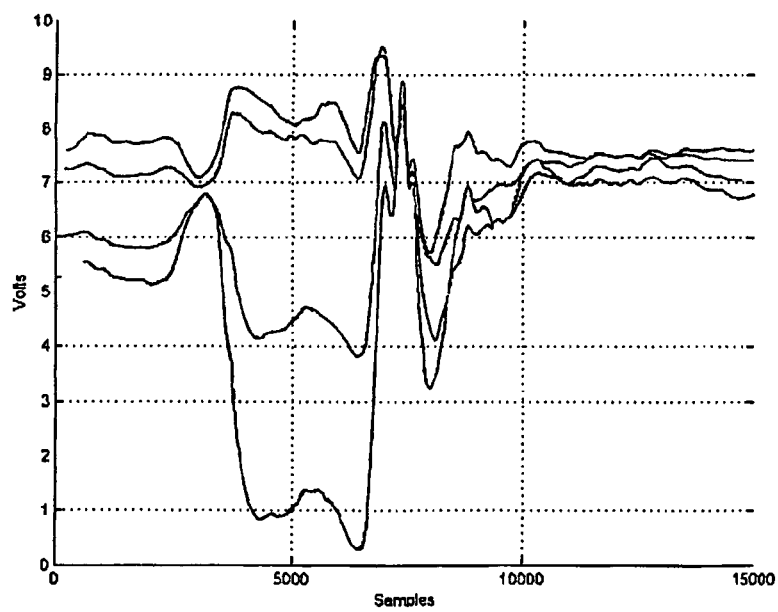
Figure 6:
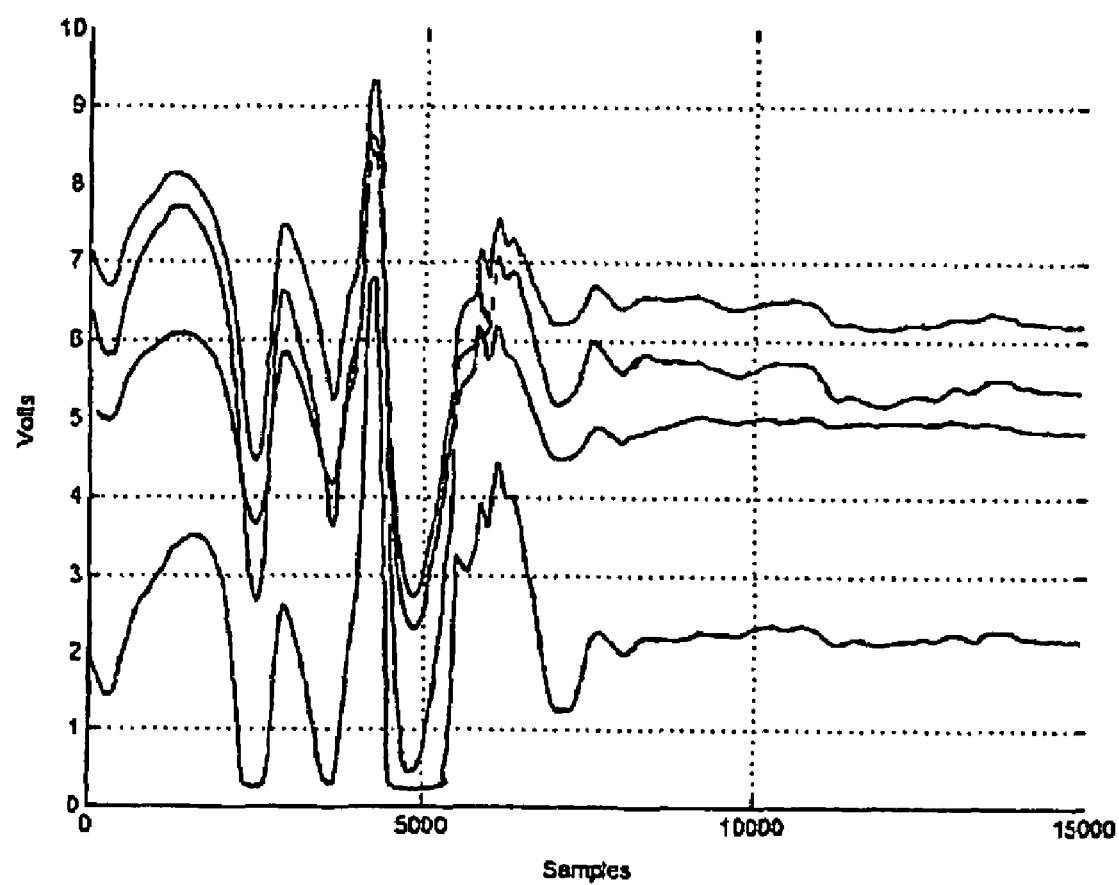

Embodiments of the invention will now be described by way of example only, with reference to the accompanying drawings in which:

FIG. 1 is a schematic representation of a generic system in accordance with the present invention, FIG. 2 is a schematic representation of a sensing system in accordance with the present invention, FIG. 3 shows the output from the system of FIG. 2 under a load, FIG. 4 is a schematic representation of another sensing system in accordance with the present invention, FIGS. 5 and 6 shows the output from the system of FIG. 4 under different loads.

Referring to FIG. 1, a generic system in accordance with the present invention comprises a surface 2 upon which a load 4 is applied, a plurality of sensors 6 coupled to the surface, a signal processor 8 to which the output from the sensors 6 is passed and an output display 10.

The system relies on the transmission of the response of the surface 2 to the contacting load 4 by the corresponding deformation of the surface continuum to strategically positioned sensor locations. The sensors 6 are used to detect local deformation or strain. By combining the sensor outputs as a simultaneous vector of inputs to the processor 8, a computer algorithm is used to determine descriptors that describe the load 4 as an output. The descriptors are those factors by which the load can be recognised by a user for output to the display 10, logging system or automated system for control of a process. The system can use both static and transient behaviour of the surface and sensing elements to describe the static and dynamic behaviour of the applied loads. The algorithm is usually a software function installed on a computer that is able to transpose the vector of inputs to the vector of descriptors of the output in 'Real Time'. For example, such functions can include fuzzy tools, neural networks and Karhunen Loève modal analysis.

An advantage of this sensing system is that there is strong coupling between the sensory data outputs, linked by the non-linear deformation behaviour of the surface. This means that relatively few sensory positions are needed to characterise the load (typically 4 to 5 on a flat surface), although additional sensory points can be used to increase redundancy in the system.

EXAMPLE 1

Referring to FIG. 2, a sensing system in accordance with the invention comprises a load bearing element 20 having substantially planar upper 22 and lower sidewalls 24 which are mutually spaced by a short distance and a peripheral sidewall 26 which extends between the upper and lower sidewalls 22,24 around their periphery and is sealed therewith whereby to define an enclosed space 28 between the upper and lower sidewalls 22,24. The upper sidewall 22, which serves as the sensing surface in use, is made from a resiliently deformable flexible material with a relevant bending stiffness to the load bearing in the application which is capable of deforming when subjected to a load 36. The lower side wall 24 serves as the base of the load bearing element 20 and for this embodiment is relatively rigid and homogeneous (homogeneity is important for reproducibility). In this case, the upper sidewall 22, the lower sidewall 24, and peripheral sidewall 26 are made from soft wood.

The enclosed space 28 is filled with a compressible porous medium such as silicone tubing with a Young's modulus of about $2.5 \times 10^6$ Pa for small loads (0-6N), and a flowable medium 30, in this case a viscous incompressible fluid such as silicone or water. It will be understood that in other embodiments other flowable mediums may be employed (e.g. oil, polymers or rubber compounds). In further embodiments, the silicone tubing is replaced by a sponge, or the silicone tubing is provided with flow restrictors. Also contained within the enclosed space 28 are three mutually spaced pressure transducers 32 which output a voltage according to changes in pressure at the transducer location. The transducers 32 are securely fixed in position between the upper and lower surfaces 22,24. In alternative embodiments (not shown) other transducers are used, for example transducers whose output is dependent on the distance between the upper and lower sidewalls 22,24 at the transducer location. The transducers 32 are electrically connected to a computer with display 34 which is loaded with the necessary algorithms.

In use, when a load 36 is applied externally to the sensing surface 22 of the load bearing element 20, the sensor surface 22 deforms and locally compresses the porous medium within the enclosed space 28. In turn, this compression causes the liquid 30 within the enclosed space 28 to flow by a diffusion process. The pressure transients caused by the compression/liquid flow are measured at the transducers 32 and output as voltages varying with time. It will be understood that the pressure transients measured will be affected by the impedance to flow of the liquid 30, the elasticity/deformability of the sensing surface 22 and the nature and structure of the porous medium. In embodiments where the fluid medium is not 100% liquid, then the compliance of the fluid volume is also an influencing factor.

In one experiment, the system was configured to determine the position of the applied load 36 in one dimension. Pressure differentials were measured at the three transducer positions, with a typical set of transients being shown in FIG. 3. Using these simultaneous measurements it was possible to work in the frequency domain to determine the amplitudes, phases and specific frequencies representing these transients using a Fast Fourier Transform (FFT) algorithm. Alternatively, information can be derived through the investigation of phase shifts and amplitude magnitudes between signals. These values were input into a trained neural network with a single output of position of the load. Using this simple approach, the measurement of position was to within 2% of the full range and was independent of load value.

EXAMPLE 2

Referring to FIG. 4, the system is similar to that illustrated in FIG. 2. Four transducers 40 are employed and the load bearing element 42 is a flexible plastics sheet, but metal (e.g. aluminium), wood and chipboard may also be used. The transducers 40 are strain gauges attached to the undersurface of the load bearing element 42, and they output a voltage dependent upon local bending forces applied to the load bearing element 42. The load bearing element 42 is mounted in a supporting frame 44.

A significant advantage of the systems of the present invention is that they allow three dimensional dynamic motion remote from the system to be analysed solely through the forces applied at the load bearing surface.

Determination of the Efficacy of Body Motion in Golf

In this application, the system of FIG. 4 was used to infer the kinetics and kinematics of a user practicing a golf swing from the reactive force transients under the feet. The system is able to determine the transients of pressure distribution beneath the feet through the response of the flexible load bearing sheet 42. The user stepped onto the flexible sheet 42 which deflects principally in bending. Upon swinging the golf club, the flexible sheet 42 transmitted its response by transient deflections at the transducer sensing positions. A typical data set is shown in FIG. 5 for a golf driving swing. Based on the spatial-time data, estimates of the perturbations from the norm or ideal approach can be obtained by the evaluation of parameters that describe the deviation in the motion. Using a neural network, the perturbations from the ideal motion can be quantified in terms of the errors in the motion of the body. In this way, it is possible to identify flaws in the technique of the user and to automatically offer advice for improvement. A similar approach can be adopted for other types of activity, such as a racquet swing (a typical dataset for a badminton racquet swing being shown in FIG. 6), for gait information on a treadmill or dance technique on a dance floor.

For such multiple data time series for a single swing, it is possible to automatically partition the transient into distinct periods of the process and to evaluate the parameters describing the kinematics and kinetics of movement. For repetitive signals, such as in gait or repetitive racquet swings it is possible to apply other non-linear analysis such as Karhunen Loève modal analysis to evaluate non-linear model parameters relating the simultaneous sensory time-series data to the motion of the body directly.

The above example demonstrates that the system can be designed to discriminate types of causes of changing loads, such as the type of motion of a human subject. Even though human subjects have different stature, the features of the changing transients in time, rather than values, are similar, and therefore can be used to distinguish different grades, categories or types of motion. Thus, for example, in sporting or health applications, where the subject will be standing, it is possible to use differences and timed separation and relative magnitude of features, such as peaks, in the combined set of sensory transients, to differentiate variations in a particular motion or between different types of motion being performed.

The sensing systems of the present invention have a wide range of utility including but not limited to:

Determination of sport performance. The system can be incorporated into the belt of a treadmill for example, or as a mat where locomotion is not to be investigated.

Determination of body performance in diagnostic and rehabilitation processes from gait or sway and balance.

Recognition of foot conditions such as perturbations from the norm in pressure distribution caused by, for example, peripheral angiopathy (in diabetes)

Security recognition systems to discriminate hand, foot and gait imprints.

In leisure activities such as sport, monitoring and training systems such as in dance, karate, aerobics, gymnasium fitness equipment can be configured as a floor system.

The same systems as for monitoring humans can be implemented to monitor animals for sport and health purposes.

Livestock monitoring for position and the transients of gait.

Traffic monitoring systems as an instrumented section of road, even some bridges. Load distribution in vehicles.

Recognition of vehicle type, vehicle wheel loading, vehicle speed, density of traffic, state of suspension, tyre contact conditions, passenger type, operator recognition, operator consciousness. Control panels/surfaces.

Redundant sensory key pad systems, keyboards, mouse pointing pads can be manufactured from non-electrical and non-metallic parts.

In manufacturing processes, particularly in food and pharmaceutical processes the system is ideal for monitoring weight, position and size on static and moving surfaces.

In healthcare applications:

Surgery: flexible endoscopes, flexible laparoscopes, flexible tunnels for MIS, palpation information, remote navigation through tactile sensation. Maintaining contact pressures between tools and devices, and tissues. At the micro/nano scale, measuring contact between devices and cells.

Medicine: Hand size, shape, gesture and grip information, spinal shape. Performance in physiotherapy. Measurement and comparison of stance before and after surgery (Joint replacement), active implant and prosthetic devices operating from tactile feedback.

The invention claimed is:

1. A sensing system comprising:
a deformable load bearing surface,
a plurality of mutually spaced sensors, said sensors being coupled through the deformation response of the surface to an applied load whereby to receive local sensory data from said surface,
a processor operatively coupled to said sensors and arranged to receive said sensory data from the sensors and to transform said sensory data into information data relating to a load applied to the surface, and an output for outputting the information data,
wherein the processor is arranged to process the sensory data received by all the sensors collectively.

2. The system as claimed in claim 1, wherein the information data has a non-linear relationship with the sensory data.

3. The system as claimed in claim 1, wherein said sensors are transducers.

4. The system as claimed in claim 3, wherein said transducers are resistive, optical, Hall effect, capacitance, proximity, or pressure differential based transducers.

5. The system as claimed in claim 3, wherein the transducers are physically connected to or in contact with the surface.

6. The system as in claim 1 wherein the system comprises a display device for displaying the information data.

7. The system as in claim 1 wherein the output of the system serves as an input for a logging system or an automated system for controlling a specific process.

8. The system as in claim 1 wherein the processor incorporates an algorithm or other interpretation function, such as a neural network or a matrix manipulation technique which receives the sensory data and applies a non-linear transform to produce the information data.

9. The system as in claim 1 wherein the deformable load bearing surface is resiliently deformable and/or elastic.

10. The system as in claim 1 wherein the deformable load bearing surface forms part of a housing, the sensors being sealed therein.

11. The system as in claim 1 wherein the housing contains a flowable material which flows within or under the surface as part of the mechanism of the deformation response of the surface, and the sensors are arranged to detect pressure differentials due to the flow of material.

12. The system as claimed in claim 1 wherein the housing also comprises one or more flow restrictors which affect the flow characteristics of the flowable material upon deformation of the surface.

13. The system as in claim 1 wherein the surface is planar.

14. A golf swing analyser comprising the system of claim 1.

15. A method of characterising a load applied to a load bearing surface comprising the steps of:
  (i) generating sensory data about the surface from a plurality of sensing elements operably coupled with the surface,
  (ii) combining the sensory data into a single vector of inputs for a transformation,
  (iii) applying a transformation to the vector of inputs whereby to generate information data characterising the load, and
  (iv) outputting the information data.

16. The method as claimed in claim 15, wherein said transformation of step (iii) is a non-linear transformation.

17. A carrier medium carrying a computer executable software program for controlling a computer to carry out steps (ii) and (iii) of claim 15.

18. The carrier medium of claim 17, wherein said carrier medium is a storage medium, such as a floppy disk, CD-ROM, DVD or a computer hard drive.

* * * * *